United States Patent
Ishikawa et al.

(10) Patent No.: US 7,648,714 B2
(45) Date of Patent: Jan. 19, 2010

(54) FOOD FOR SKIN MOISTURE RETENTION

(75) Inventors: Junko Ishikawa, Haga-gun (JP); Yutaka Takagi, Haga-gun (JP); Tomoko Nomura, Haga-gun (JP)

(73) Assignee: Kao Corporation, Tokyo (JP)

( * ) Notice: Subject to any disclaimer, the term of this patent is extended or adjusted under 35 U.S.C. 154(b) by 472 days.

(21) Appl. No.: 11/194,520

(22) Filed: Aug. 2, 2005

(65) Prior Publication Data
US 2006/0029643 A1 Feb. 9, 2006

(30) Foreign Application Priority Data
Aug. 5, 2004 (JP) ............................. 2004-229322
Aug. 5, 2004 (JP) ............................. 2004-229323

(51) Int. Cl.
*A61K 31/685* (2006.01)
*A61K 47/00* (2006.01)

(52) U.S. Cl. ......................... 424/439; 514/78

(58) Field of Classification Search ................. 424/439; 514/78
See application file for complete search history.

(56) References Cited

U.S. PATENT DOCUMENTS

| | | | |
|---|---|---|---|
| 5,723,497 A | 3/1998 | Ohashi et al. | |
| 6,896,896 B2 | 5/2005 | Miyanishi et al. | |
| 2003/0044449 A1 | 3/2003 | Miyanishi et al. | |
| 2004/0001792 A1 | 1/2004 | Biatry | |
| 2004/0009284 A1 * | 1/2004 | Boice et al. | 426/601 |

FOREIGN PATENT DOCUMENTS

| | | | |
|---|---|---|---|
| JP | 361271205 A | * | 12/1986 |
| JP | 402270813 A | * | 11/1990 |
| JP | 4-300825 | | 10/1992 |
| JP | 05-320069 | | 12/1993 |
| JP | 6-271446 | | 9/1994 |
| JP | 11-113530 | | 4/1999 |
| JP | 02000139345 A | * | 5/2000 |
| JP | 2001-64170 | | 3/2001 |
| JP | 2002-275046 | | 9/2002 |
| JP | 2002-281936 | | 10/2002 |
| JP | 2002-320447 | | 11/2002 |
| JP | 2002326920 A | * | 12/2002 |
| JP | 2003-2835 | | 1/2003 |
| JP | 2003-171310 | | 6/2003 |
| JP | 2004-67676 | | 3/2004 |
| JP | 2006-516280 | | 6/2006 |
| WO | WO 2004/064820 | | 8/2004 |

OTHER PUBLICATIONS

Fragrance Journal, vol. 23, No. 1, 1995, pp. 81-89, (with partial English translation).
Fragr.,vol. 25(1), pp. 90-44, 1997 (with English abstract).
Shokuhin to Kaihatsu (Foods and Developments), vol. 36(8), pp. 9-11, 2001.

* cited by examiner

*Primary Examiner*—Sreeni Padmanabhan
*Assistant Examiner*—Sahar Javanmard
(74) *Attorney, Agent, or Firm*—Oblon, Spivak, McClelland, Maier & Neustadt, L.L.P.

(57) ABSTRACT

This invention relates to a food containing a glycosylated ceramide and diacylglycerol. This food is capable of improving and enhancing the barrier function of skin and increasing water holding capacity of the skin.

8 Claims, No Drawings

FOOD FOR SKIN MOISTURE RETENTION

FIELD OF THE INVENTION

This invention relates to a food for improving and enhancing the barrier function of skin, thereby promoting the water holding function of the skin.

BACKGROUND OF THE INVENTION

Stratum corneum of a skin has the function of cutaneous barrier, thereby suppressing evaporation of water from the body and protecting the body from the exterior stimuli. This barrier function is easily damaged by UV, surfactant, dryness, mechanical stimulation, activated oxygen, residual chlorine in tap water and the like, and such damage in the skin barrier is known to induce dry skin, atopic dermatitis, rough skin and the like.

Various means that improve such a barrier function have been reported. Among these means, there are methods to be carried out by the external administration of a plant extract such as Arnica or turmeric (JP-A-2003-171310), and the external administration of polysaccharides such as pamaquine and pachymaran (JP-A-2002-275046).

The stratum corneum of mammalian (including human) skin is also known to contain a considerable level of ceramides consist of fatty acids and sphingoid bases and these substances are thought to have the function of preventing evaporation of water from the body. Attempts have also been made to improve the water holding function of the stratum corneum by administering such ceramide and sphingosine.

JP-A-1994-271446 discloses effectiveness of the application on the skin of sphingosines in reducing wrinkles controlling.

However, systemic application of such an external medication is difficult to continue for consecutive days, and also could induce inflammation, stimulus, allergic reaction and the like. In the meantime, systemic application can be readily achieved if the medication is administered by oral ingestion.

For example, Fragrance Journal, 23(1), 81(1995) describes enhancement of water holding function of the skin by oral ingestion of the ceramide, and JP-A-1999-113530 describes skin treatment and cosmetic effects realized by the oral ingestion of the ceramide. JP-A-2003-2835 describes that the absorption is improved when the sphingoglycolipid is ingested with a plant sterol, and such improvement is manifested by increase in the water holding capacity of the stratum corneum as well as amelioration of the skin roughness. However, oral ingestion of the components as mentioned above has so far failed to show sufficient water holding and barrier function of the skin.

With regard to the diacylglycerol, JP-A-1992-300825 discloses its function of suppressing the increase of the neutral fat in blood, and JP-A-2001-64170 discloses its function of increasing blood HDL cholesterol. Accordingly, diacylglycerols are used in cooking oils and various other food products produced by using oil or a fat.

In spite of the situation as described above, no food has so far been known that contain both the diacylglycerol and the glycosylated ceramide. Effectiveness of oral ingestion of sphingolipids in improving the barrier function and the water holding function remains to be unknown, and so does oral ingestion of sphingolipids.

SUMMARY OF THE INVENTION

This invention provides a food containing a glycosylated ceramide and a diacylglycerol.

The present invention also provides a food containing a sphingosine analog represented by the following general formula (1):

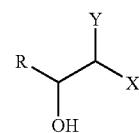

wherein R represents a hydrocarbon group containing 1 to 40 carbon atoms which is substituted or unsubstituted with hydroxyl group, X represents —$CH_2OH$, —$CO_2H$, or

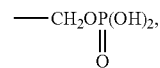

and Y represents —$NH_2$, —$NHCH_3$, —$N(CH_3)_2$, or

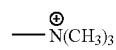

The present invention also provides a method for improving the barrier function of the skin, which comprises ingestion of glycosylated ceramide and diacylglycerol.

The present invention also provides a method for improving the barrier function of the skin, which comprises ingestion of a sphingosine analog represented by the general formula (1) as described above.

The present invention also provides a method for improving water holding function of the stratum corneum, which comprises ingestion of glycosylated ceramide and diacylglycerol.

The present invention also provides a method for improving the water holding function of the stratum corneum, which comprises ingestion of a sphingosine analog represented by the general formula (1) as described above.

DETAILED DESCRIPTION OF THE INVENTION

This invention provides food products which exhibit remarkable action of improving the barrier function of skin and which is capable of promoting water holding function of the skin after their ingestion.

The inventors of the present invention investigated various components which may improve skin water holding function after its ingestion, and thus arrived at the finding that not only increase in the ceramide content of the stratum corneum, but also marked improvements in the barrier function of the skin and the water holding function of the stratum corneum are induced by the ingestion of glycosylated ceramide together with diacylglycerol, or by the ingestion of a particular sphingosine analog.

The food product of the present invention is capable of readily improving and enhancing the barrier function of the entire skin and increasing the skin water holding capacity.

The term "glycosylated ceramide" used in the present invention designates a ceramide having at least one glycosyl residue bounded thereto, and examples of such glycosylated ceramide include glucosylceramide and galactosylceramide. Ceramide is a substance formed by the amide linkage of a sphingoid base to a fatty acid.

The glycosylated ceramide may be obtained by extraction from the tissue of a mammal such as cow or horse, or from plants such as rice bran and the like, or by chemical synthesis. For example, glylcosyl ceramide can be obtained from rice (Agric. Biol. Chem., 49, 2753 (1985)), rice bran (JP-A-1987-187404, and JP-A-1999-279586), wheat (Agric. Biol. Chem., 49, 3609 (1985), and JP-A-1994-507653), soybean (Chem. Pharm. Bull., 38 (11), 2933 (1990), and JP-A-1995-2683), konjak (JP-A-2003-2835), and other legumes and grain and root crops.

Alternatively, the glycosylated ceramide may be a commercially available product such as Nippn ceramide (manufactured by Nippon Flour Mills Co., Ltd), oryza ceramide (manufactured by Oryza Oil & Chemical Co, Ltd.), Nissan ceramide (manufactured by NOF Corporation), or Ceramide (manufactured by Unitika).

The diacylglycerol used in the food products of the present invention is preferably diacylglycerol in which the constituent fatty acid has an acyl group containing 8 to 24 carbon atoms, and in particular, 12 to 22 carbon atoms such as those derived from palmitic acid, stearic acid, oleic acid, linoleic acid, eicosapentaenoic acid, or docosahexaenoic acid. Proportion of the unsaturated acyl group in the diacylglycerol is preferably at least 55% by weight (hereinafter simply referred to as "%"), and at least 70% of all acyl groups. More preferably, the unsaturated fatty acid contains 15 to 85% of oleic acid and 15 to 85% of linoleic acid.

The diacylglycerol may be obtained by the method described in JP-A-1992-300825 or the like, for example, by transesterification of a triglyceride oil such as rapeseed oil, soybean oil, rice bran oil, corn oil, palm oil, olive oil, shiso oil, sesame oil, perilla oil, linseed oil, or fish oil with glycerin, or by esterification between a fatty acid from a lipid and glycerin. Exemplary reaction methods include chemical reactions using an alkaline catalyst and biochemical reactions by using a lipolytic hydrolase such as lipase. Among them, a biochemical reaction is preferred from the viewpoint of the appearance.

Such diacylglycerol cannot promote the barrier function of the skin or water holding function of the stratum corneum by itself. However, when a diacylglycerol is incorporated in a food product together with a glycosylated ceramide, amount of the ceramide in the stratum corneum is increased, and the barrier function of the skin as well as the water holding function of the stratum corneum are remarkably improved (Example 1).

The glycosylated ceramide and the diacylglycerol are incorporated in the food of the present invention containing the glycosylated ceramide and the diacylglycerol preferably at a blend ratio of 100:1 to 1:10000, and more preferably at 10:1 to 1:100 in weight ratio.

The amount of the glycosylated ceramide and the diacylglycerol incorporated is preferably 0.01 to 20%, and more preferably, 0.1 to 10%.

The sphingosine analog used in the food of the present invention is the one represented by the general formula (1) as described above. In the general formula (1), the hydrocarbon group represented by R may be either saturated or unsaturated, and examples include 1-pentadecenyl, pentadecyl, 1-hydroxypentadecyl, 1-heptadecenyl, heptadecyl, 1-hydroxyheptadecyl, methyl, ethyl, 1-nonenyl, 1-undecenyl, 1-tridecenyl, 1-nonadecenyl, 11-hydroxyheptadecyl, 13-hydroxynonadecyl, 9-methylhexadecyl, and 11-methyloctadecenyl. Among these, 1-hydroxyalkyl such as 1-hydroxypentadecyl or 1-hydroxyheptadecyl is classified into phytosphingosine, and use of such phytosphingosine is preferred in the present invention.

Four stereoisomers (D-erythro form, D-threo form, L-erythro form, and L-threo form) are known for the sphingosine analog (1), and any one of such isomers or any combination of such isomers may be used in the food product of the present invention.

Of the sphingosine analogs (1) used in the present invention, natural sphingosine analogs may be obtained by extracting sphingolipid, ceramide, or the like from an appropriate tissue such as plant, yeast, or bovine brain, and after hydrolyzing the extract, further extracting with an organic solvent.

The sphingosine analog (1) may be synthesized by the method described in Journal of the American Chemical Society (J. Am. Chem. Soc.), vol. 95, page 4098 (1973), Journal of Lipid Research (J. Lipid Res.), vol. 19, page 250 (1978), Tetrahedron Letters (Tetrahedron Lett.), vol. 29, page 239 (1988), Tetrahedron, vol. 42, page 5961 (1986), and the like. Furthermore, the N-methyl form, N,N-dimethyl form, and N,N,N-trimethyl form may be synthesized by N-methylating such sphingosine by the method described, for example, in Biochemistry, vol. 7, page 2192 (1968).

The food of the present invention containing the sphingosine analog may preferably further contain diacylglycerol (1) as described above for the sake of further improving the barrier function of the skin and the water holding function of the stratum corneum.

In such case, the sphingosine analog (1) and the diacylglycerol are preferably incorporated in the food product at a weight ratio of 100:1 to 1:10000, and more preferably at 10:1 to 1:100.

The incorporated amount is preferably 0.01 to 10%, and more preferably 0.1 to 5%.

The food of the present invention may be prepared by mixing the glycosylated ceramide and the diacylglycerol as described above, or the sphingosine analog (1) as describe above which may be preferably mixed with the diacylglycerol, with an additives such as sweetener, colorant, antioxidant, vitamin, flavor, mineral and the food matrix such as protein, lipid, carbohydrate, dietary fiber, or the like, and this mixture may be made into various forms of food products by any method commonly used in the art.

Exemplary forms of the food produced include liquid beverages such drink, powder beverages such as powder juice, confectioneries such as candy, drops, jelly, cookies, chocolate, cakes, yogurt, and chewing gum, seasonings, cooking oils, dairy products, breads, and modified rice. Also included are cosmetic and health food in the form of tablets, capsules, granules, or the like and pet foods for dogs, cats, hamsters, and the like.

The food of the present invention may be ingested at an adequately selected amount depending on the form of the food as well as age, sex, and other conditions of the consumer. The amount of ingestion, however, is about 0.1 µg to 2 mg, and preferably about 2 µg to 400 µg in terms of the glycosylated ceramide or the sphingosine analog (1) per kg body weight per day, and administration can be once or divided in 2 to 4 times.

As will be described in the section of the Examples, the food of the present invention acts to increase the amount of ceramide in the stratum corneum to thereby improve the barrier function of the skin as well as the water holding function of the stratum corneum. Accordingly, when ingested according to the above, this food has many benefits such as enhanced barrier function of the skin, the improved water holding function of the stratum corneum, the prevention or amelioration of the dry skin, prevention of the skin trouble caused by such dry skin, and prevention or amelioration of the atopic dermatitis.

Accordingly, the food of the present invention may be used as a food having various functions, for example, as a food capable of improving the barrier function of the skin, or as a cosmetic or health food capable of improving the water holding function of the skin, thereby preventing or ameliorating the dry skin, or preventing or ameliorating the atopic dermatitis.

EXAMPLES

Example 1

Production of a Food Containing a Glycosylated Ceramide

Food products having a glycosylated ceramide incorporated therein were produced. Their composition was as shown in Table 1.

Water was added to Nippn ceramide (manufactured by Nippon Flour Mills Co., Ltd), a diacylglycerol (DAG manufactured by Kao Corporation), caseine, DL-methionine, corn starch, pregelatinized corn starch, sucrose, cellulose powder, corn oil, AIN-76 mineral mix, AIN-76A vitamin mix, and choline bitartrate (the foregoing products being the products of Oriental Yeast Co., Ltd.), and after kneading with heat, the mixture was extrusion molded and dried to produce the Product 1 of the present invention. Comparative product 1 was produced by repeating the procedure as described above without using the diacylglycerol, and a control food product was also produced by repeating the procedure as described above without using the diacylglycerol or the Nippn ceramide.

TABLE 1

Unit, g

| Blend ratio (%) | Control | Comparative product 1 | Example product 1 |
|---|---|---|---|
| Nippn ceramide (equivalent of the glycosylated ceramide) | 0 | 1.7 (0.1) | 1.7 (0.1) |
| DAG | 0 | 0 | 0.1 |
| Casein | 20 | 20 | 20 |
| DL-methionine | 0.3 | 0.3 | 0.3 |
| Corn starch | 43 | 43 | 43 |
| Corn starch (pregelatinized) | 12 | 12 | 12 |
| Sucrose | 10 | 10 | 10 |
| Cellulose powder | 5 | 5 | 5 |
| Corn oil | 5 | 3.3 | 3.2 |
| AIN-76A mineral mix | 3.5 | 3.5 | 3.5 |
| AIN-76A vitamin mix | 1 | 1 | 1 |
| Choline bitartrate | 0.2 | 0.2 | 0.2 |

Example 2

Production of a Food Containing a Sphingosine

Food products having a sphingosine incorporated therein were produced. The composition was as shown in Table 2.

Water was added to phytosphingosine (manufactured by DOOSAN Corporation), casein, DL-methionine, corn starch, pregelatinized corn starch, sucrose, cellulose powder, corn oil, AIN-76A mineral mix, AIN-76A vitamin mix, and choline bitartrate (the foregoing products being the products of Oriental Yeast Co., Ltd.), and after kneading with heat, the mixture was extrusion molded and dried to produce a dry feed (Example product 2). Example product 3 was produced by also incorporating 0.1 g of a diacylglycerol (DAG, manufactured by Kao Corporation). A control food product was also produced by repeating the procedure as described above without using the phytosphingosine or the diacylglycerol.

TABLE 2

Unit, g

| Blend ratio (%) | Control | Example product 2 | Example product 3 |
|---|---|---|---|
| Phytosphingosine | 0 | 0.1 | 0.1 |
| DAG | 0 | 0 | 0.1 |
| Casein | 20 | 20 | 20 |
| DL-methionine | 0.3 | 0.3 | 0.3 |
| Corn starch | 43 | 43 | 43 |
| Corn starch (pregelatinized) | 12 | 12 | 12 |
| Sucrose | 10 | 10 | 10 |
| Cellulose powder | 5 | 5 | 5 |
| Corn oil | 5 | 4.9 | 4.8 |
| AIN-76A mineral mix | 3.5 | 3.5 | 3.5 |
| AIN-76A vitamin mix | 1 | 1 | 1 |
| Choline bitartrate | 0.2 | 0.2 | 0.2 |

Example 3

Improvement of the Barrier Function of the Skin, and Increase in the Water and Ceramide Contents of the Stratum Corneum 6 week old female HR1 mice were used for the experiment, and the mice were preliminarily given a basic feed (solid feed of AIN-76A) and water ad libitum for 1 week before the start of the experiment. The mice were then grouped by their body weight (8 animals per group), and given the test feed as shown in Table 1 for 5 weeks.

1) Recovery of the Barrier Function of the Skin

The mice were measured for their initial TEWL (transepidermal water loss) by using a hydrometer (Meeco). The procedure of tape adhesion and removing (hereinafter referred to as the "tape stripping") using Nichiban PPS tape was repeated 5 times at the same site of the mouse skin, and immediately and two hours after the tape stripping, the TEWL were measured to calculate the degree of recovery.

2) Water Holding Function of Stratum Corneum

The Water holding function of the stratum corneum was measured by SKICON-200 (IBS Ltd) as the Skin conductance.

3) Ceramide Content (Amount of the Ceramide Per mg of the Stratum Corneum)

The animals were given the test feed for 8 weeks (8 animals per group), and then sacrificed. Epidermis from murine back was prepared by heating 60° C. for 1 minute in water bath. The epidermis was immediately incubated in trypsin solution at 37° C. for 1 hour to obtain the stratum corneum. After freeze dried and weighted, the stratum corneum lipids were extracted by Bligh and Dyer method (Bligh, E. G., and W. J. Dyer. 1959. A rapid method of total lipid extraction and purification. Can. J. Biochem. Physiol. 37:911-917), and the amount of the ceramide was determined by TLC methods.

The results are shown in Tables 3 and 4.

TABLE 3

|  | Control group | Group administered with comparative product 1 | Group admininistered with Example product 1 |
| --- | --- | --- | --- |
| Water holding function of the stratum corneum (Skin conductance: μS) | 161.7 | 176.3 | 201.9 |
| Recovery of the barrier function (%) | 30.7 | 43.3 | 55.4 |
| Amount of ceramide per mg of the corneum layer (μg) | 14.4 | 18.5 | 22.1 |

TABLE 4

|  | Control group | Group administered with Example product 2 | Group administered with Example product 3 |
| --- | --- | --- | --- |
| Water holding function of the stratum corneum (Skin conductance: μS) | 161.7 | 220.4 | 269.6 |
| Recovery of the barrier function (%) | 30.7 | 61.2 | 71.0 |
| Amount of ceramide per mg of the corneum layer (μg) | 14.4 | 23.7 | 23.6 |

As shown in these tables, the group administered with comparative product 1 containing glycosylated ceramide showed subtle effects of improving the water holding function of the stratum corneum and enhancing the barrier recovery function as compared to the group administered with the control. In contrast, the group administered with the Example product 1 of the present invention containing both the glycosylated ceramide and the diacylglycerol showed an increased amount of the ceramide in the stratum corneum, and significant enhancement of the increase in the moisture content of the stratum corneum and the recovery of barrier function.

Ingestion of the Example product 2 of the present invention containing a sphingosine analog resulted in an increase in the amount of the ceramide in the stratum corneum as well as a significant increase in the water holding function of the stratum corneum and enhancement of the recovery of barrier function compared to the group administered with the control which does not contain the sphingosine analog. In the case of the Example product 3 of the present invention having the sphingosine analog and the diacylglycerol incorporated, the effect of enhancing the increase in the water holding capacity of the stratum corneum and the recovery of barrier function was even more significant than the Example product 2 of the present invention.

What we claim is:

1. A food comprising at least one glycosylated ceramide and at least one diacylglycerol in which the constituent fatty acid has an acyl group comprising 8 to 18 carbon atoms.

2. A food comprising (a) at least one sphingosine analog represented by the following formula (1):

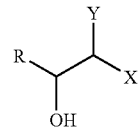

(1)

wherein R represents a hydrocarbon group containing 1 to 40 carbon atoms which is substituted or unsubstituted with hydroxyl group, X represents —CH$_2$OH, —CO$_2$H, or

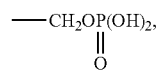

and Y represents —NH$_2$, —NHCH$_3$, —N(CH$_3$)$_2$, or

and (b) at least one diacylglycerol.

3. The food according to claim 1 or 2, wherein the food is a food that improves the barrier function of the skin.

4. The food according to claim 1 or 2, wherein the food is a food that improves the water holding function of the skin.

5. A method for improving the water holding function of the stratum corneum comprising ingestion of a glycosylated ceramide and diacylglycerol.

6. A method for improving the water holding function of the stratum corneum comprising ingestion of (a) sphingosine analog represented by the following general formula (1):

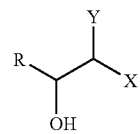

(1)

wherein R represents a hydrocarbon group containing 1 to 40 carbon atoms which is substituted or unsubstituted with hydroxyl group, X represents —CH$_2$OH, —CO$_2$H, or

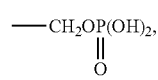

and Y represents —NH$_2$, —NHCH$_3$, —N(CH$_3$)$_2$, or

and (b) at least one diacylglycerol.

7. The food according to claim 1, wherein the constituent fatty acid is oleic acid or linoleic acid.

8. The food according to claim 1, wherein the unsaturated fatty acid in said diacylglycerol comprises from 15 to 85% of oleic acid and from 15 to 85% of lenoic acid.

* * * * *

UNITED STATES PATENT AND TRADEMARK OFFICE
CERTIFICATE OF CORRECTION

PATENT NO.        : 7,648,714 B2
APPLICATION NO.   : 11/194520
DATED             : January 19, 2010
INVENTOR(S)       : Ishikawa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 991 days.

Signed and Sealed this

Twenty-third Day of November, 2010

David J. Kappos
*Director of the United States Patent and Trademark Office*